United States Patent [19]
Yan

[11] Patent Number: 5,911,452
[45] Date of Patent: Jun. 15, 1999

[54] APPARATUS AND METHOD FOR MOUNTING A STENT ONTO A CATHETER

[75] Inventor: John Y. Yan, Sunnyvale, Calif.

[73] Assignee: Advanced Cardiovascular Systems, Inc., Santa Clara, Calif.

[21] Appl. No.: 08/795,335

[22] Filed: Feb. 4, 1997

[51] Int. Cl.⁶ ............................. B23P 11/00; B23P 19/04
[52] U.S. Cl. ................ 29/516; 623/1; 606/194; 606/108; 606/1; 29/282; 425/392
[58] Field of Search .................. 29/516, 407.08, 29/282, 280, 715; 606/108; 425/318, 391, 392

[56] References Cited

U.S. PATENT DOCUMENTS

| | | |
|---|---|---|
| 696,289 | 3/1902 | Williams . |
| 4,468,224 | 8/1984 | Enzmann et al. ............... 604/247 |
| 4,576,142 | 3/1986 | Schiff ............................ 128/1 |
| 4,644,936 | 2/1987 | Schiff ............................ 128/1 |
| 4,681,092 | 7/1987 | Cho et al. ...................... 128/1 |
| 4,697,573 | 10/1987 | Schiff ............................ 128/1 |
| 4,901,707 | 2/1990 | Schiff ............................ 128/1 |
| 4,907,336 | 3/1990 | Gianturco . |
| 5,132,066 | 7/1992 | Charlesworth et al. . |
| 5,133,732 | 7/1992 | Wiktor . |
| 5,183,085 | 2/1993 | Timmermans . |
| 5,189,786 | 3/1993 | Ishikawa et al. . |
| 5,437,083 | 8/1995 | Williams et al. . |
| 5,546,646 | 8/1996 | Williams et al. ............... 29/407.08 |
| 5,626,604 | 5/1997 | Cottone, Jr. .................... 606/198 |
| 5,630,830 | 5/1997 | Verbeek . |
| 5,653,691 | 8/1997 | Rupp et al. ..................... 604/96 |
| 5,738,674 | 4/1998 | Williams et al. ................ 606/1 |
| 5,746,764 | 5/1998 | Green et al. .................... 606/194 |
| 5,783,227 | 7/1998 | Dunham ......................... 425/318 |
| 5,785,715 | 7/1998 | Schatz ............................ 606/108 |

FOREIGN PATENT DOCUMENTS

| | | |
|---|---|---|
| EP 0 630 623 | 12/1994 | European Pat. Off. . |
| EP 0 697 226 | 2/1996 | European Pat. Off. . |
| 159065 | 2/1921 | United Kingdom . |
| WO 98/14120 | 4/1998 | WIPO . |
| WO 98/19633 | 5/1998 | WIPO . |

OTHER PUBLICATIONS

U.S. Patent Application Serial No. 08/795,335 filed Feb. 4, 1997.

U.S. Patent Application Serial No. 08/837,771 filed Apr. 22, 1997.

U.S. Patent Application Serial No. 08/089,936 filed Jul. 15, 1997.

U.S. Patent Application Serial No. 08/962,632 filed Nov. 3, 1997.

*The eXTraordinary Stent*, C.R. Bard Brochure (Undated).

*Primary Examiner*—S. Thomas Hughes
*Assistant Examiner*—John Preta
*Attorney, Agent, or Firm*—Fulwider Patton Lee & Utecht, LLP

[57] ABSTRACT

A system for loading a stent onto a catheter is disclosed. The system includes a housing having an internal chamber with a flexible tube extending therethrough. A stent is positioned at about a mid portion of the flexible tube, and the balloon portion of the catheter is inserted into the flexible tube and positioned within the stent. Pressurized fluid is injected into the internal chamber thereby circumferentially compressing the flexible tube and in turn compressing the stent and crimping it onto the balloon portion of the catheter. A balloon folding attachment can be mounted onto an end of the housing. The inner lumen of the attachment has progressively varying cross-sectional shapes that fold the flattened balloon portion of the catheter as it is advanced into the attachment. The folded balloon portion is continually advanced into the attachment into the flexible tube until it is aligned within the stent.

17 Claims, 2 Drawing Sheets

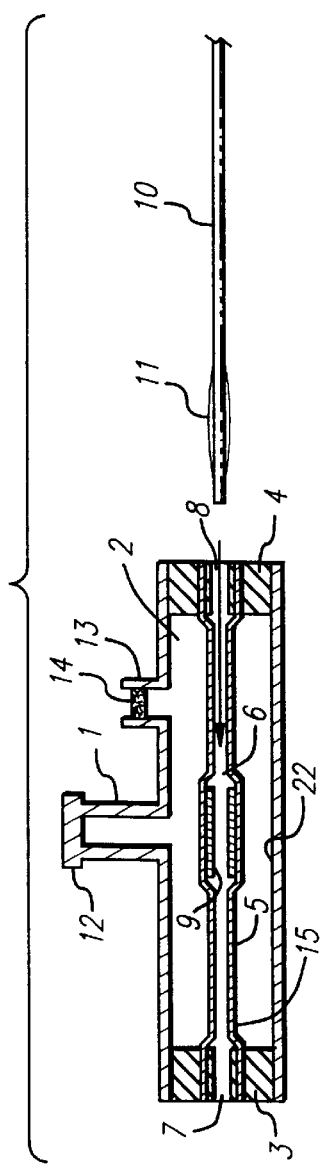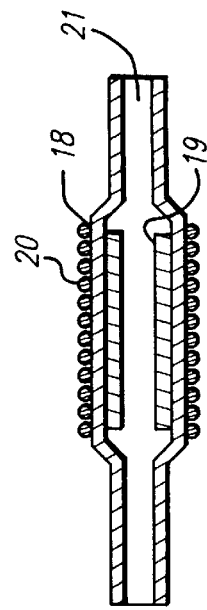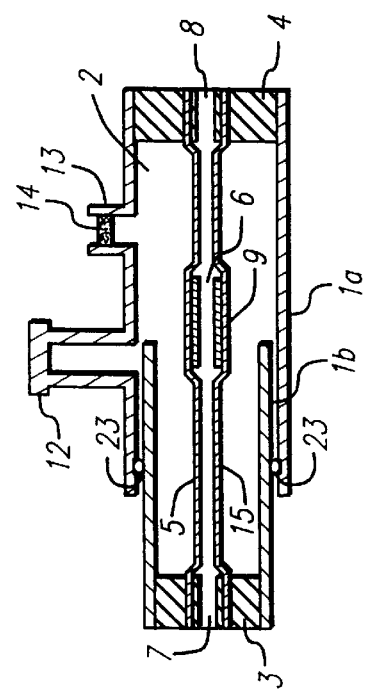

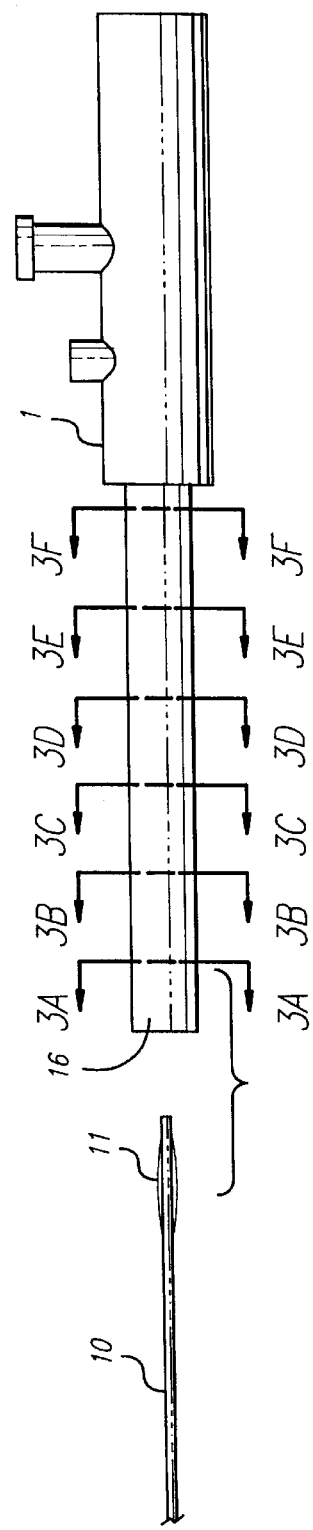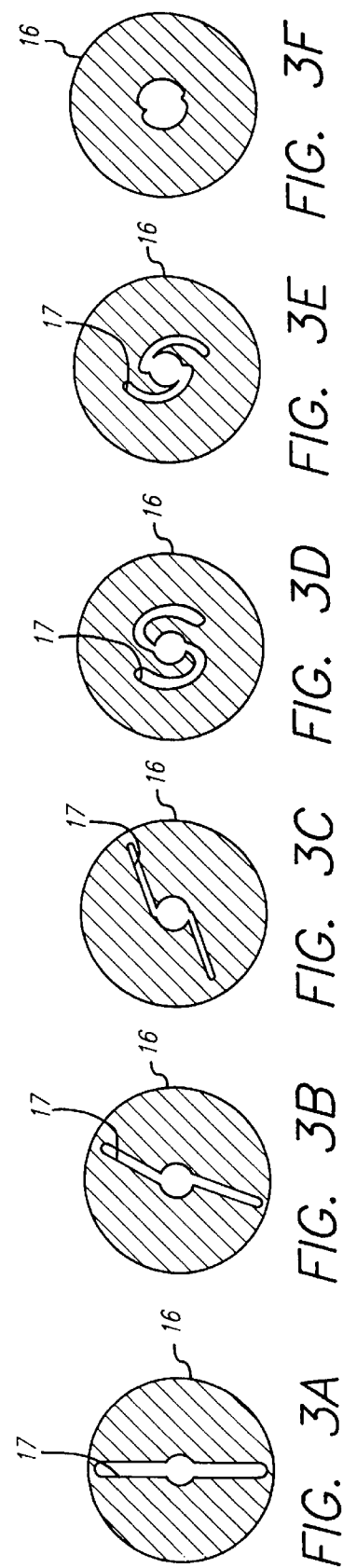

APPARATUS AND METHOD FOR MOUNTING A STENT ONTO A CATHETER

BACKGROUND OF THE INVENTION

The present invention relates to an apparatus for loading a tubular graft, such as a stent, onto a catheter assembly. Such a catheter assembly can be, for example, of the kind used in typical percutaneous transluminal coronary angioplasty (PTCA) procedures.

In typical PTCA procedures, a guiding catheter is percutaneously introduced into the cardiovascular system of a patient through the brachial or femoral arteries and advanced through the vasculature until the distal end of the guiding catheter is in the ostium. A guide wire and a dilatation catheter having a balloon on the distal end are introduced through the guiding catheter with the guide wire sliding within the dilatation catheter.

The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall, thereby dilating the lumen of the artery. The balloon is then deflated to a small profile, so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis may occur in the artery, which may require another angioplasty procedure, a surgical bypass operation, or some other method of repairing or strengthening the area. To reduce the likelihood of restenosis and to strengthen the area, an intravascular stent is implanted for maintaining vascular patency. The stent is typically transported through the patient's vasculature where it has a small delivery diameter, and then is expanded to a larger diameter, often by the balloon portion of the catheter. The stent also may be of the self-expanding type.

Since the catheter and stent will be traveling through the patient's vasculature, and probably through the coronary arteries, the stent must have a small, delivery diameter and must be firmly attached to the catheter until the physician is ready to implant it. Thus, the stent must be loaded onto the catheter so that it does not interfere with delivery, and it must not come off of the catheter until it is implanted in the artery.

In conventional procedures where the stent is placed over the balloon portion of the catheter, it is necessary to crimp the stent onto the balloon portion to reduce its diameter and to prevent it from sliding off the catheter when the catheter is advanced through a patient's vasculature. Non-uniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing blood clots in the vasculature, including thrombosis. Thus, it is important to ensure the proper crimping of a stent onto a catheter in a uniform and reliable manner.

This crimping is often done by hand, which can be unsatisfactory due to the uneven application of force, again resulting in non-uniform crimps. In addition, it is difficult to judge when a uniform and reliable crimp has been applied. Some self-expanding stents are difficult to load by hand onto a delivery device such as a catheter. Furthermore, the more the stent is handled, the higher the likelihood of human error which would be antithetical to crimping the stent properly. Hence, there is a need in the art for a device for reliably crimping a stent onto a catheter.

There have been mechanisms devised for loading a stent on to a catheter. For example, U.S. Pat. No. 5,437,083 to Williams et al. discloses a stent-loading mechanism for loading a stent onto a balloon delivery catheter of the kind typically used in PTCA procedures. The device comprises an arrangement of plates having substantially flat and parallel surfaces that move in rectilinear fashion with respect to each other. A stent carrying catheter can be crimped between the flat surfaces to affix the stent onto the outside of the catheter by relative motion between the plates. The plates have multiple degrees of freedom and may have force-indicating transducers to measure and indicate the force applied to the catheter during affixation of the stent.

Williams et al. also discloses a stent-loading device comprising an elongated tubular member having an open end and a sealed off end. The tubular member houses an elastic bladder which extends longitudinally along the inside of the tubular member. The tubular member and bladder are designed to hold a stent that is to be loaded onto a balloon catheter assembly. Upon placement of the stent over the balloon portion of the catheter, a valve in the loading device is activated to inflate the bladder. The bladder compresses the stent radially inward onto the balloon portion of the catheter to a reduced diameter to thus achieve a snug fit.

Although the above-described methods by which stents are crimped are simple, there is a potential for not crimping the stent sufficiently tight to prevent it from loosening in the tortuous anatomy of the coronary arteries. Because the amount of compression needed to be applied by the fingers will vary with the (a) strength of the operator, (b) day-to-day operation, (c) catheter and balloon material and configuration, (d) experience of the operator in crimping, and (e) other factors, the tightness in which the stent is crimped onto a balloon catheter may vary considerably.

Indeed, because of these factors, the tightness follows a normal or Chi square distribution. At the lower tail end of the distribution, the stents will be loose and susceptible to movement on the balloon during insertion. At the higher tail end, the stent will be too tight and will affect the expansion characteristics (i.e., a dog bone effect) of the balloon.

In view of the foregoing, there is a need for a stent crimping device that reliably and uniformly crimps stents onto the balloon portion of a catheter.

SUMMARY OF THE INVENTION

The present invention is directed to a stent loading system and method for crimping a stent onto a catheter, and preferably onto a balloon catheter. The system comprises a housing having opposite ends forming an internal chamber, a port disposed on the housing in fluid communication with the internal chamber, and a flexible tube extending through the internal chamber and passing through the opposite ends of the housing, wherein the flexible tube includes a hollow interior and open ends, and wherein the stent is disposed within the hollow interior.

A pressurized fluid is injected through the port into the chamber. As this fluid fills the internal chamber, the flexible tube undergoes radial compression. When the balloon portion of the catheter is inserted into the open end of the flexible tube and into the stent, the pressurized fluid compresses the flexible tube reducing its diameter and thereby compressing the stent onto the balloon portion of the catheter.

In one embodiment of the present invention, a balloon folding attachment is connected to the housing end. In particular, the balloon folding attachment has a body with an interior passage therethrough that has progressively changing cross-sectional shapes and which is in communication with one opening of the flexible tube, and wherein the balloon portion of the catheter is inserted through the interior passage and is progressively folded into a desired shape.

Furthermore, the housing may include an optional second port having a hydrophobic filter, which filter allows air or gases to pass, but not liquids. While the internal chamber is filled with a fluid, the ambient gas within the internal chamber bleeds out through the filter.

Accordingly, the present invention provides a mechanism for uniformly crimping a stent onto a balloon portion of a catheter wherein the applied radial force on the stent is consistent and precise. The tightness of which the stent is crimped onto the balloon catheter can therefore be carefully controlled.

Another advantage of the present invention is that the housing and other parts can be readily made from a disposable material. In this embodiment, the stent can be preloaded inside the flexible tube and packaged and sterilized. The package is then ready for use by the cath lab physician when a stent needs to be mounted on a catheter of the physician's choice.

Alternatively, the stent can be loaded onto the balloon portion of the catheter and slightly crimped. Thereafter, the combination of the stent and balloon catheter are inserted into the flexible tube where the final crimping step takes place. Furthermore, the ports in the housing can be a Luer type, to be adaptable to the equipment already available to the physician.

In another embodiment, the housing is made from a shape memory alloy material. The housing wraps around the flexible tube that houses the stent. When a catalyst such as heat is applied to the shape memory alloy housing, the housing shrinks in size and compresses the flexible tube thereunder. In turn, the compressed flexible tube crimps the stent onto a balloon catheter inserted therein. Removing the heat from the shape memory alloy material of the housing causes the housing to restore to its initial size and shape, thus permitting withdrawal of the crimped stent and catheter combination.

These and other advantages of the invention will become apparent from the following detailed description thereof when taken in conjunction with the accompanying exemplary drawings.

BRIEF DESCRIPTION OF THE DRAWINGS

FIG. 1 is a side elevational view of a preferred embodiment of the present invention shown in a cross-section depicting the housing, flexible tube, stent, and catheter with a balloon portion, just prior to insertion.

FIG. 2 is a side elevational view showing the present invention with a balloon folding attachment connected thereto.

FIG. 3 is a series of cross-sectional views in which FIG. 3A through FIG. 3F are cross-sectional views taken along lines A—A through F—F of FIG. 2.

FIG. 4 is a cross-sectional view depicting an alternative embodiment of the invention wherein the housing is formed of a shaped memory alloy capable of contracting and crimping the stent onto a catheter.

FIG. 5 is a cross-sectional view depicting an alternative embodiment wherein the length of the housing is adjustable.

DETAILED DESCRIPTION OF THE PREFERRED EMBODIMENTS

The present invention is directed to a stent loading system for mounting a stent onto a balloon portion of a catheter. Beneficially, the present invention system facilitates controlled, repeatable, crimping pressure to be applied to a stent when the latter is loaded onto a balloon portion of a catheter. While the invention is described in detail as applied to the coronary arteries, those skilled in the art will appreciate that it can be applied to devices for use in other body lumens as well, such as peripheral arteries and veins. Also, although the invention is described with respect to mounting a stent on the balloon portion of a catheter, the invention is not so limited and includes mounting stents or grafts on any type of catheter used to deliver and implant such stents. Where different embodiments have like elements, like reference numbers have been used.

FIG. 1 provides a side elevational view of a preferred embodiment of the present invention stent loading system wherein the device is shown in a cross-section to depict the interior construction. As seen in this figure, housing 1 has a preferably long, cylindrical shape and includes internal chamber 2. The opposite ends of housing 1 are sealed to completely enclose internal chamber 2. To seal the opposite ends, in the preferred embodiment, housing 1 is enclosed by press fit seals 3,4.

A flexible tube 5 is stretched across internal chamber 2, and inner lumen 6 of flexible tube 5 is in communication with openings 7, 8 formed in press fit seals 3, 4. An uncrimped stent 9 is positioned at about the midsection of flexible tube 5 within inner lumen 6. The inner surface of inner lumen 6 is close to and perhaps in loose fitting contact with the outer surface of uncrimped stent 9.

In a preferred embodiment, uncrimped stent 9 is inserted into inner lumen 6 of flexible tube 5 and is expanded slightly to enlarge its inside diameter. In this manner, the slightly enlarged inside diameter of stent 9 allows easy clearance of catheter 10 to be inserted therein. Furthermore, the preexpansion step stretches flexible tube 5, thereby securing stent 9 within tube 5. This condition is shown in FIG. 1.

As mentioned above, the present invention system is adapted for use with a PTCA balloon catheter 10 having balloon portion 11 at the distal end. Of course, the present invention can be used with a balloon catheter of any conventional design known in the art as well as any catheter without a balloon.

In the preferred embodiment, an adapter with a male-threaded Luer fitting (not shown) is used as an inflation port. A syringe, an inflation/deflation device commonly referred to as an "indeflator," a compressed fluid source, or any pressurized source known in the art, is attached to inflation port 12. This serves as the inlet for the pressurized fluid that fills internal chamber 2.

In an alternative embodiment, inflation port 12 can include a three-way stopcock (not shown) that is connected to the Luer fitting. Thus, a saline filled syringe or indeflator is connected to the inlet of the stopcock. Fluid is injected by the syringe into internal chamber 2 and air within the internal chamber 2 is purged through an extra side port on the three-way stockcock.

It is possible to have more than one port connected to internal chamber 2 of housing 1. One of these optional ports 13 can be connected to hydrophobic filter 14. This filter 14 permits a gas such as air to pass, but seals in liquids such as saline. Therefore, while internal chamber 2 is filled with saline, air bleeds out through hydrophobic filter 14. This mechanism aids the user in purging air from the system.

Yet another port (not shown) can be used for monitoring internal pressures. Still another port can be used for fluid input or output. As mentioned earlier, the ports in the housing can be a Luer type, straight tubes, threaded tubes, etc.

Internal chamber 2 can be pressurized with different fluids as well as gases. The fluid is preferably saline. The gases can be, for example, compressed air, nitrogen, argon, or helium.

As disclosed, housing 1 includes inflation port 12 for funneling a pressurized fluid into internal chamber 2 to compress flexible tube 5. Internal chamber 2 is otherwise sealed from the ambient atmosphere, while inner lumen 6 of flexible tube 5 is open to the ambient atmosphere by virtue of openings 7, 8. Since flexible tube 5 has openings 7, 8, it is uniformly compressed by the pressurized fluid. Furthermore, because neither end of flexible tube 5 is exposed to the fluid, uncrimped stent 9 placed within flexible tube 5 does not experience an axial pressure which would otherwise distort the tubular shape of stent 9 during the crimping process.

The novel stent crimping method is described in the following manner. In the preferred method, inflation port 12 includes a Luer fitting, and as described above, the outlet of a three-way stopcock is connected to the Luer fitting. A saline-filled syringe or indeflator is connected to the inlet of the stopcock. Using the syringe, fluid can be injected into internal chamber 2 and air within internal chamber 2 will be purged therefrom through an extra side port on the three-way stopcock.

In keeping with the preferred method, any lubricant or lubricious coatings are removed from the exterior surface of catheter balloon 11 with a cleaning fluid such as isopropyl alcohol. Stent 9 is preloaded into flexible tube 5 prior to crimping. Stent 9 can optionally be slightly expanded by any conventional methods to ensure clearance with the outside diameter of balloon 11 of catheter 10.

Catheter 10 is inserted into inner lumen 6 and advanced toward the midsection of flexible tube 5 through opening 8 in the direction of the arrow shown in FIG. 1. Ideally, catheter 10 is inserted so that balloon 11 is centered directly within stent 9. As explained in greater detail below, alignment of balloon portion 11 to stent 9 is accomplished visually.

With balloon portion 11 in position within stent 9, fluid is injected into internal chamber 2. Because the internal pressure is evenly distributed over chamber wall 22 and outer surface 15, flexible tube 5 is compressed radially inwardly against stent 9. Further, because of open ends 7, 8 in flexible tube 5, no fluid pressure is exerted on the ends of flexible tube 5 and there are no axial forces applied to stent 9 during the crimping step. In fact, stent 9 experiences fairly homogeneous, radial pressures tending to uniformly crimp stent 9 onto balloon portion 11. In a preferred embodiment of the present invention, the required amount of pressure inside internal chamber 2 is expected to exceed ten atmospheres. Once the crimping process is complete, the inflation fluid can be withdrawn from inside internal chamber 2 by use of the syringe or by drainage through one of the ports.

Housing 1 is preferably made from a transparent material so that the alignment of stent 9 relative to balloon portion 11 can be observed continuously. Materials such as polycarbonate, PVC, polysulfone, metals, metal alloys, ceramic, or the like can be used as well. Obviously with opaque materials, a window can be formed in housing 1. Without an observation window or transparent housing, it is still possible to gage the relative position of the balloon to the stent by using depth indicators or markers on the catheter.

In the preferred embodiment, balloon portion 11 is folded into a cylindrical shape so that it can be inserted into inner lumen 6 of flexible tube 5 without hanging or binding. The folding of balloon portion 11 can be achieved through any process known in the art.

In an alternative embodiment, the present invention provides balloon folding attachment 16, shown in FIG. 2, mounted on housing 1. A deflated balloon portion 11 is inserted into balloon folding attachment 16 and advanced therealong to fold the flat, outer expanse of the balloon into a tightly wrapped cylinder, just prior to inserting the balloon within stent 9 for subsequent crimping. To do this, balloon folding attachment 16 has a unique internal lumen 17 configuration, shown in progressive cross-sections A through F of FIG. 3. The cross-sections of internal lumen 17 show progressively changing cross-sectional shapes that guide a relatively flattened balloon portion 11 inserted therein, as it is advanced through lumen 17, to wrap around itself to form a cylinder. This is apparent from the drawings of sections 3A—A through 3F—F.

To use balloon folding attachment 16, balloon portion 11 of catheter 10 is flattened on its outer periphery. The flattened balloon 11 is inserted through inner lumen 17 of attachment 16. As balloon portion 11 is advanced into inner lumen 17, the interior walls of inner lumen 17 guide and twist the outer periphery of flattened balloon portion 11. When the process begins, flattened balloon portion 11 has a cross-sectional shape that resembles a propeller. As the balloon portion 11 travels through the varying cross-sections, the outstretched propeller blades are wrapped around a central axis, conceptually speaking. This type of folding pattern allows for even expansion of balloon portion 11 when it is inflated, and is necessary for uniformity of the stent expansion when it is deployed. Of course, other patterns may be possible depending on the internal lumen configuration of balloon folding attachment 16.

Once folded balloon portion 11 passes through attachment 16, it enters inner lumen 6 of flexible tube 5. The process of crimping stent 9 on to folded balloon portion 11 then proceeds as described earlier. The crimped stent tends to hold the now tightly folded balloon 11 in its low-profile configuration for intraluminal delivery.

Balloon folding attachment 16 can be made from plastics, metals, ceramics, or other materials. It can be made by molding, machining, or other methods known in the art. It is attached to housing 1 through mechanical attachments, threads, adhesives, or can be formed into the housing.

Flexible tube 5 can be sealed into housing 1 by different means. The preferred method is to press flexible tube 5 against the two press fit seals 3, 4. Press fit seals 3, 4, in turn, can be joined to housing 1 mechanically through friction, threads, or by solvent welding, adhesives, ultrasonic welding, or the like.

In the preferred embodiment, the uncrimped but slightly expanded stent 9 is pre-assembled within flexible tube 5 and the entire combination is packaged together. The stent and housing combination thus packaged can be sterilized and shipped together to the end user. After the stent is crimped onto the catheter of choice, the flexible tube package is discarded. All tools needed to use the present invention are commonly found in a cath lab or a hospital. Lastly, no special skills are needed to use the present invention to load a stent onto a balloon catheter.

In an alternative embodiment, the present invention system provides a housing, internal chamber, and flexible tube as before. On the other hand, there is no stent that is preloaded into the flexible tube. Rather, the stent is loaded manually onto the balloon catheter. Through means known in the art, such as by hand crimping, the stent is slightly crimped onto the balloon catheter. In this alternative process, the stent that is preloaded onto the catheter is then inserted into the inner lumen of the flexible tube. Fluid is injected into the internal chamber, as described, to further crimp the stent onto the balloon portion of the catheter.

In another alternative embodiment, shown in FIG. 4, there is a flexible tube 18 with preloaded stent 19 positioned at about a midportion thereof. Wrapped along the exterior of flexible tube 18 is housing 20 which is in the form of a coil, tube, roll, or similar shape. In this alternative embodiment, housing 20 is made from a shape memory alloy material such as Nitinol. When this alloy is subjected to temperatures at or above the alloy's transitional temperature, housing 20 shrinks, thereby compressing flexible tube 18 and in turn crimping stent 19 onto the balloon catheter, which has been inserted into inner lumen 21.

FIG. 5 provides a cross-sectional view of yet another alternative embodiment of the present invention. A key feature is the adjustable length of housing 1, which is split into housing sections 1a and 1b. Sections 1a and 1b are assembled coaxially and telescopically. Optional seal or O-ring 23 is positioned in between the overlapping sections 1a and 1b to provide a smooth telescoping action, and to minimize leakage of any fluid from internal chamber 2.

This embodiment permits adjustment of the axial length of the housing. One benefit derived from this construction is that variations in length of stent 9 can be accommodated. Also, during the crimping process, additional pressure exerted on stent 9 can be created by forcing section 1b into section 1a, thereby reducing the internal volume occupied by the fluid. The fluid, depending on its compressibility, exerts a reactive force on flexible tube 5 which, in turn, exerts a crimping force on stent 9.

Once the heat source is removed from housing 20, the housing restores to its original size and shape, permitting removal of the stent and balloon catheter combination therefrom. If a coiled housing configuration were used, and because the metal material of the housing 20 is highly elastic, it can be uncoiled rather easily so that tube 18 can be removed to release the balloon catheter with the crimped stent thereon.

Other modifications can be made to the present invention without departing from the scope thereof. The specific dimensions and materials of construction are provided as examples, and substitutes are readily contemplated which do not depart from the invention.

What is claimed is:

1. A stent loading system for mounting a stent on a catheter, comprising:
    a housing having opposite ends forming an internal chamber;
    a port associated with the housing in fluid communication with the internal chamber;
    a flexible tube extending through the internal chamber and passing through the opposite ends of the housing, wherein the flexible tube includes a hollow interior and open ends, and wherein the stent is disposed within the hollow interior;
    a pressurized fluid injected through the port into the chamber;
    a balloon folding attachment connected to the housing end, the attachment having a body with an interior passage therethrough that has progressively changing cross-sectional shapes and is in communication with one opening of the flexible tube, and wherein a balloon portion of the catheter is inserted through the interior passage and is progressively folded into a desired configuration; and
    wherein the catheter is inserted through the balloon folding attachment and into the open end of the flexible tube and into the stent, and the pressurized fluid compresses the flexible tube radially inwardly thereby compressing the stent on to the catheter.

2. The stent loading system according to claim 1, wherein the catheter has a balloon associated with the balloon portion so that the stent is mounted on the balloon.

3. The stent loading system according to claim 1, wherein the progressively changing cross-sectional shapes include a circle with radially extending legs, a circle with radially extending curved legs, and a circle with curved legs that tangentially intersect the circle.

4. The stent loading system according to claim 1, wherein the progressively changing cross-sectional shapes include a silhouette of a twin opposed propeller blades on a circular rotor wherein the blades progressively twist around the rotor.

5. The stent loading system according to claim 1, wherein the port includes a Luer type valve.

6. The stent loading system according to claim 1, wherein the housing includes a second port in communication with the internal chamber, the second port having a hydrophobic filter.

7. The stent loading system according to claim 6, wherein the internal chamber includes a gas that is expelled through the hydrophobic filter.

8. The stent loading system according to claim 1, wherein the housing and flexible tube are at least partially formed from a transparent material.

9. The stent loading system according to claim 1, wherein the flexible tube further comprises a mid-section having an enlarged diameter to hold the stent therein.

10. A stent loading system for mounting a stent onto a balloon portion of a catheter comprising:
    a housing having an internal chamber;
    a flexible tube passing at least partially through the housing and the internal chamber, wherein the stent is disposed inside the flexible tube;
    a port in fluid communication with the internal chamber;
    a fluid injected through the port into the internal chamber to compress the flexible tube and the stent;
    a balloon folding attachment connected to the housing wherein the folding attachment includes an interior passage in communication with the flexible tube, the interior passage having progressively varying cross-sectional shapes that sequentially twist the balloon portion into a folded cylindrical shape when inserted therein; and
    wherein the balloon portion of the catheter is inserted through the balloon folding attachment and into the stent inside the flexible tube, and the fluid injected into the internal chamber compresses the flexible tube which in turn compresses the stent onto the balloon portion of the catheter.

11. The stent loading system of claim 10, wherein the progressively varying cross-sectional shapes include a circle with radially extending straight legs that progressively wrap around the circle.

12. A method for loading a stent onto a balloon at a distal end of a catheter, the method steps comprising:

providing a housing having an internal chamber;

providing a flexible tube passing at least partially through the housing and the internal chamber;

positioning the stent inside the flexible tube;

providing a port in the housing in fluid communication with the internal chamber;

providing a balloon folding attachment connected to the housing, wherein the attachment includes an interior passage with progressively changing cross-sectional shapes in communication with the flexible tube;

inserting the balloon into the balloon folding attachment and through the interior passage, thereby forming a folded balloon;

inserting the folded balloon at the distal end of the catheter into the stent; and injecting a fluid through the port into the internal chamber to compress the flexible tube and in turn compress the stent onto the folded balloon at the catheter distal end.

13. The method according to claim 12, further comprising the steps of withdrawing the fluid through the port, and removing the folded balloon of the catheter from the flexible tube with the stent mounted thereon.

14. The method according to claim 12, wherein the step of inserting the balloon into the balloon folding attachment comprises a step of folding the balloon into a cylindrical shape.

15. The method according to claim 12, further comprising the steps of providing a gas inside the internal chamber, providing a port with a hydrophobic filter in the housing in communication with the internal chamber, and expelling the gas through the hydrophobic filter as the fluid is injected into the internal chamber.

16. The method according to claim 14, wherein the steps of inserting the balloon into the balloon folding attachment comprises the steps of flattening the balloon portion and folding the balloon into a cylindrical shape.

17. The stent loading system according to claim 1, wherein the housing includes at least two sections coaxially disposed to provide a telescoping action.

* * * * *

UNITED STATES PATENT AND TRADEMARK OFFICE
CERTIFICATE OF CORRECTION

PATENT NO. : 5,911,452
DATED : Jun. 15, 1999
INVENTOR(S) : John Y. Yan

It is certified that error appears in the above-identified patent and that said Letters Patent is hereby corrected as shown below:

Title page under FOREIGN PATENT DOCUMENTS, add the following cited patent:
--159,065       02/1921         Great Britain--.

Column 10, claim 16, line 17, change "14", to read --12--.

Signed and Sealed this

Second Day of November, 1999

Attest:

Attesting Officer

Q. TODD DICKINSON

Acting Commissioner of Patents and Trademarks